United States Patent [19]

Reif

[11] 4,250,625
[45] Feb. 17, 1981

[54] MINIATURE BLADE DEVICE

[76] Inventor: Alfred Reif, Silcherstrasse 21, 7446 Oberboihingen, Fed. Rep. of Germany

[21] Appl. No.: 66,185

[22] Filed: Aug. 13, 1979

[51] Int. Cl.³ .............................................. A61B 17/00
[52] U.S. Cl. ...................................... 30/383; 128/317
[58] Field of Search ................ 30/381, 382, 383, 386; 128/317

[56] References Cited

U.S. PATENT DOCUMENTS 2,618,298   11/1952   Pratt ...................................... 30/386

FOREIGN PATENT DOCUMENTS 2615301   10/1977   Fed. Rep. of Germany ........... 128/317
2640267    5/1978   Fed. Rep. of Germany ............. 30/383

*Primary Examiner*—Jimmy C. Peters

[57] ABSTRACT

A blade device for motor-driven cutter instruments has a one-piece cutter bar with a smooth external edge, a sprocket wheel, an endless chain with chain links which meshes with the sprocket wheel and is guided on the cutter bar, and aligned with its central plane narrow, sharpened cutting elements on the outside of the chain links. One type of chain link is a slider which slides on the external edge of the cutter bar and has a lagging zone which meshes with the sprocket wheel and two passage holes arranged close to its base. The second type of chain link is two opposed trapezium-shaped very thin laminae on both sides of the cutter bar, with corner zones which cover the passage holes in the slider and two pins rigidly laser-connected, which pass through the passage holes.

10 Claims, 4 Drawing Figures

MINIATURE BLADE DEVICE

The invention relates to a miniature blade device for motor-driven cutting instruments which comprises a cutter bar, a sprocket wheel which is provided at the motor end of the cutter bar and is aligned with the cutter bar, an endless chain which comprises chain links and meshes with the sprocket wheel and is guided on the circumference of the cutter bar so as to be aligned with the central plane of the cutter bar, as well as sharpened, extremely narrow cutting elements which are provided on the outside of the chain links.

BACKGROUND OF THE INVENTION

Such blade devices are described, for example, in DE OS Nos. 2 611 720 or 2 660 077. They allow entirely new cutting qualities and work possibilities to be achieved in medical practice as well as in everyday use, instead of the surgical knife, the bone saw and the cautery used so far. Good cutting qualities are attained without the absolutely steady hand of those who are less talented so that the pressure of work experienced by real experts in their field can be reduced. If the cutting elements are saws, cutting widths of 1 mm are achieved, for example in bone surgery. This results in cut bones being shortened to a lesser extent, cut edges becoming smoother and healing being accelerated. This type of blade device also prevents accidents during operations, such as the intestinal explosion described in the Danish "Weekly publication for doctors" in July 1978, which resulted in death.

However, such blade devices can also be advantageously used in entirely different fields, for example in micro-surgery, grafting of plants, cutting of cakes, amateur handiwork and so on.

A problem of the known devices consists in the fact that the cutter bar of the blade device has several layers. Two external cheeks are necessary, and between the external cheeks there are provided small rotatable guide wheels or stationary guide surfaces. This sandwich construction is expensive in view of the very small dimensions. The riveting-together thereof tends to warp the cutter bar. The cutter bar has on its outer circumference a groove in which the chain links run in a more or less covered manner, and it is possible for bits to settle therein, which may be a hindrance during the running of the chain itself and also during the sterilization thereof.

OBJECT AND STATEMENTS OF THE INVENTION

It is the object of the invention to indicate a blade device which is cheaper in production, allows the same miniaturization but simultaneously prevents foreign particles from settling or allows foreign particles that have settled to be easily removed. In addition, it is essentially to be possible to use the technique of press-working for the production of the blade device.

According to the invention, this problem is solved by the following features:
(a) The cutter bar is a single-piece blade having a smooth external edge which guides chain links parallel to the central plane, which chain links slide on the external edge.
(b) Apart from the sprocket wheel, no other guide wheel is provided.
(c) Two types of chain links are provided, namely a slider whose base slides on the external edge and whose lagging zone that is close to the base is designed as an engagement surface for sprockets of the sprocket wheel, which zone has approximately the width of the cutter bar and which has, at right angles to the central plane, two passage holes which are approximately evenly spaced from the base and are arranged so as to be close thereto.
(d) The second chain link type is composed of two approximately trapezium-shaped very thin laminae, whose tapering zones are inwardly directed, are arranged on both sides of the cutter bar so as to be parallel to the central plane thereof and so as to be at a short distance from the external surfaces and whose corner zones of the widening portion cover the passage holes leaving a small clearance, and two pins which pass through the passage holes and are rigidly connected to the corner zones.
(e) The pins are connected to the corner zones by lazer welding.

Moreover, the invention also includes the following advantageous features:

Every slider has a cutting element. These features ensure that directly behind each cutting element there cuts another cutting element and that the cut effected therebetween cannot be shut but is kept open. Furthermore, the load, e.g. along the passage holes and the circumferences of the pins, is then equal.

The cutting elements are saw teeth. The same basically applies to these features to which there is added the fact that if saw teeth are provided which follow one closely behind the other, a cutting depth stop may be dispensed with.

The cutting elements are knife blades. The features ensure that the invention can also be utilized for a type of knife.

The base of the slider entends up to the engagement surface in a straight and even manner. Due to these features the base attains its maximum size, the surface pressure is reduced and the passage holes can be at a maximum distance from each other.

The same engagement surface is provided on the slider in the preceding zone close to the base. The feature ensures that the sliders can be produced so as to be symmetrical about a central plane which is vertical thereto.

The edge distance of the passage holes from the base and the engagement surface of the slider is approximately equal to the thickness of the slider in that zone. The features ensure optimum conditions for the stamping tool, and thus the best possible contour accuracy for the sliders when they are stamped out, as well as little waste.

The edge distance of the passage holes from one another is approximately equal to double the thickness of the slider in that zone. The features ensure a simple stamping tool, little waste, and an even distribution of the loaded cross sections.

The laminae project approximately half-way above and half-way below the external edge of the cutter bar. The features ensure good guiding conditions.

The pins are butt-welded to the corner zones of the laminae and serve as spacers. Due to these features, passage holes in the laminae are avoided and a simpler production technique is brought about.

DESCRIPTION OF THE DRAWINGS

The invention will now be described with reference to a preferred exemplified embodiment. In the drawings.

DETAILED DESCRIPTION

Figure 2:
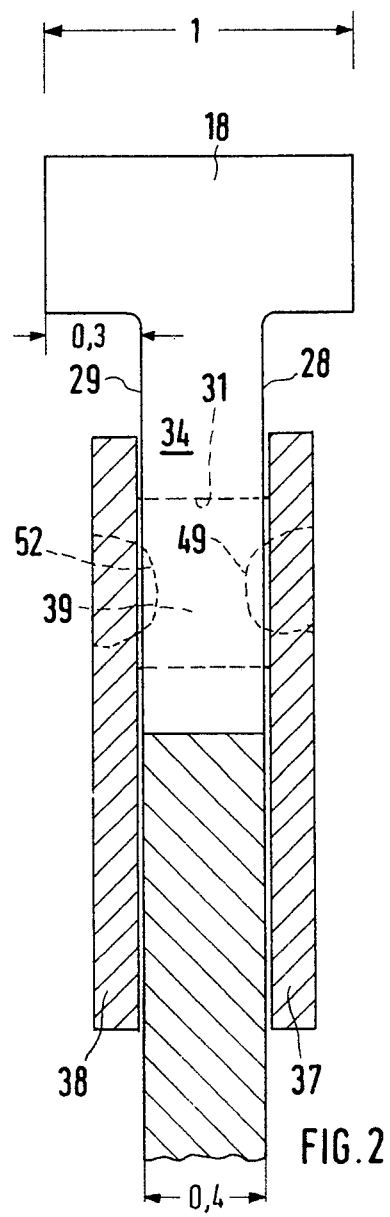
FIG. 2 shows the view of FIG. 1 from the left-hand side on the same scale.
Figure 4:
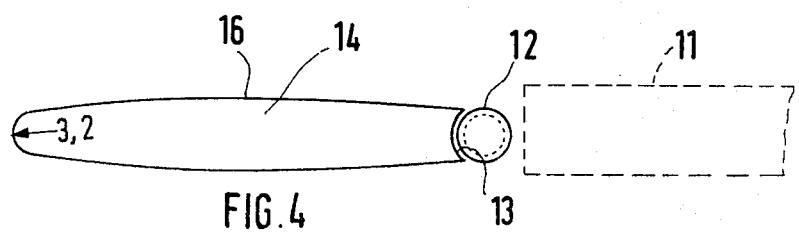
FIG. 4 shows a diagrammatical side view of a cutter bar on a scale of 1:1, without the chain and with the sprocket wheel and the handle/motor part indicated.

According to FIG. 4, the instrument has a handle part 11 (shown in broken lines) in which the motor and, if necessary, batteries are provided. This handle is connected to a driven sprocket wheel 12 through a gearing part which is not shown in detail. The sprocket wheel 12 partly projects into a conforming cut-out 13 in a cutter bar 14. The cutter bar is secured to the gearing part in a manner not shown. The cutter bar is 80 mm long and 11 mm wide at its widest point; on the left-hand side, it has a radius of 3.2 mm. Its effective cutting length is 48 mm. The rest of the length is required for the fastening of the cutter bar 14 to the handle part 11 and for a clamping device which is not shown in detail. The cutter bar 14 has a smooth external edge 16, which has been polished so as to give little friction and which, as shown in FIG. 2, is even but otherwise of course follows the contour of the cutter bar 14, as shown in FIG. 4. The cut-out 13 is not polished.

According to FIG. 2, the cutter bar is 0.4 mm thick and made of hardened steel.

Figure 1:
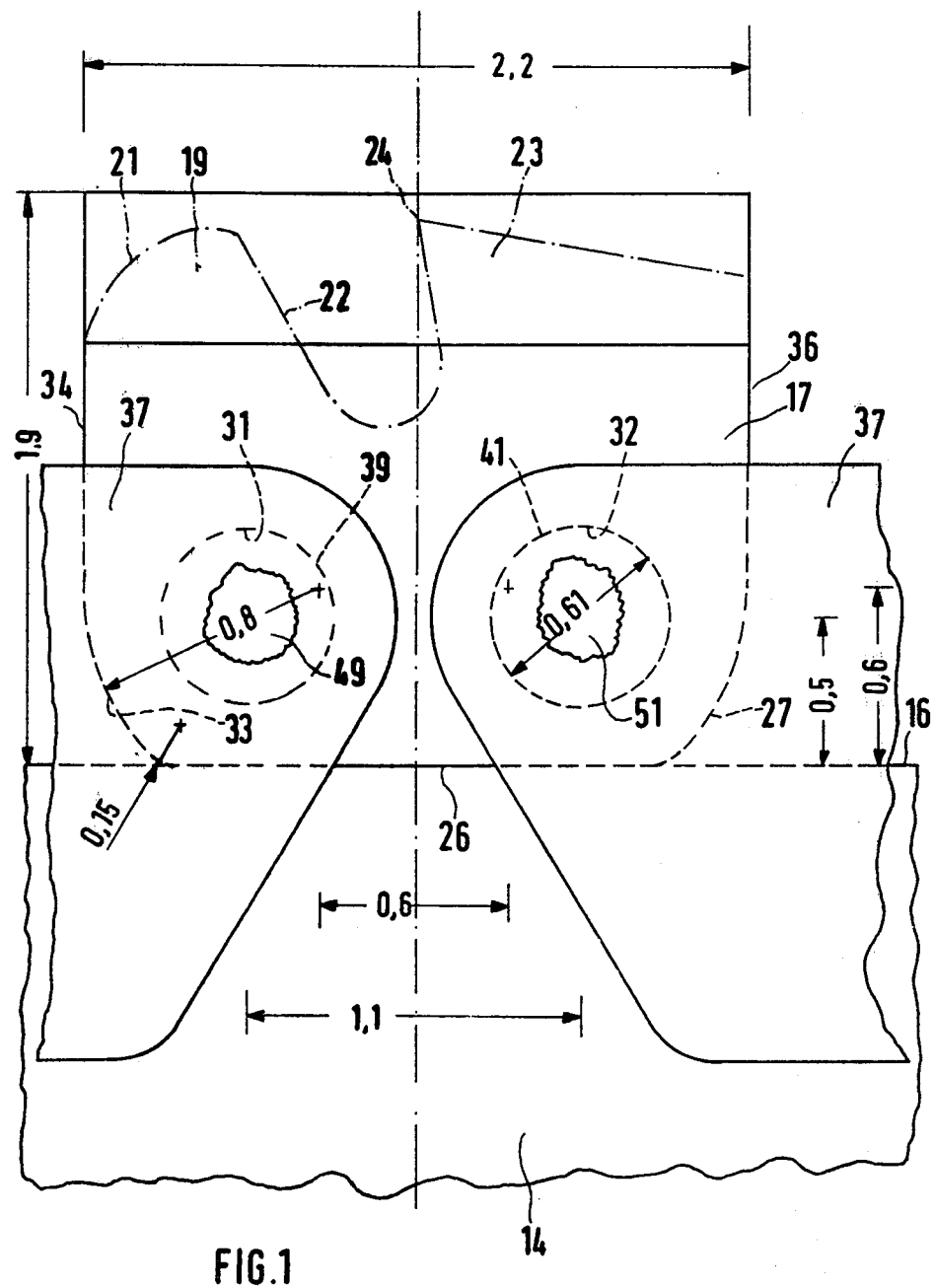
FIG. 1 shows a side view, on a scale of 50:1 and partly broken away, of a slider including an indicated cutting element, a zone of the cutter bar as well as two laminae which have been broken away.

A slider 17 has a thickness of 0.4 mm at the bottom and of 1 mm at the top in its widening 18. The cross-sectional form according to FIG. 2 is symmetrically T-shaped. The widening 18 is necessary if it is intended to realise saw teeth. If it is intended to realise knife blades, then the widening 18 is not necessary. The dash-dotted line in FIG. 1 indicates the finishing of the upper zone of the slider 17 in the event of saw teeth being provided. On the left-hand side, there is provided a cutting depth stop 19 which has an abutting surface 21 in the shape of a circle sector. This is followed by a chip groove 22 which in turn is followed by a saw tooth 23. The saw cutting edge 24 is slightly higher than the highest elevation of the abutting surface 21. As FIG. 1 shows, the cutting depth stop 19 and the saw tooth 23 are recessed from the material of the widening 18, while the chip groove 22 has been recessed both from the widening 18 and from the lower thinner zone of the slider 17. According to FIG. 1, the movement of the saw tooth 23 is from right to left and accordingly the sprocket wheel 12 rotates in the anti-clockwise sense according to FIG. 4. The lower thinner zone of the slider 17 has on its underside a completely even base 26 which has been polished so as to give little friction and which merges on the right-hand side in an engagement surface 27 which is so designed that the sprocket engaging therebehind in the area of the sprocket wheel 12 meets optimum engaging conditions. According to FIG. 1, this engagement surface 27 converges by a radius of 0.8 mm and a radius of 0.15 mm, whose centres are at the indicated points.

According to FIG. 1, the slider 17 is 2.2 mm long and 1.9 mm high. In the thinner zone of the slider 17, where it has parallel side walls 28, 29, there are provided two passage holes 31, 32 which have a diameter of 0.61 mm and whose inner surface is fine-finished. The distance of the inner surface of the passage hole 32 from the engagement surface 27 and from the base 26 is such that in the zone shown it is 0.4 mm beyond approximately 90°.

The same applies to the passage hole 31 towards the base 26 and the preceding surface 33. Relative to the lower thinner zone of the slider 17, the passage holes 31, 32 are arranged so as to be relatively deep close to the base 26 in the lower half. Their horizontal spacing is approximately two widths of material and the distance from the chip groove 22 is also sufficiently long. The front surface 34 and the rear surface 36 of the slider 37 are flat, parallel to each other and vertical to the base 26. The engagement surface 27 and possibly also the surface 33 are fine-finished. Altogether 56 sliders 17 are provided. If all the sliders 17 have saw teeth 23, there are provided 56 saw teeth 23. If, for example, it is desired to provide only every other slider 17 with a saw tooth 23, then the slider 17 is cut off horizontally beneath the widening 18.

The sliders 17 are connected together by front laminae 37 and by congruent rear laminae 38 as well as by circular cylindrical pins 39, 41.

Figure 3:
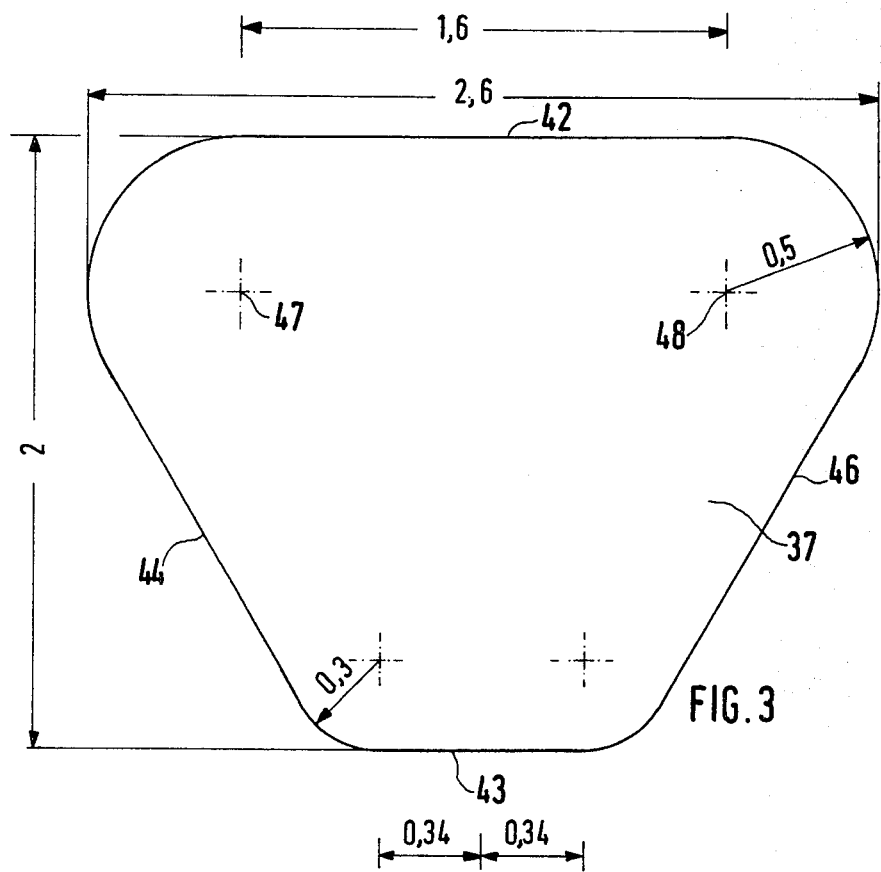
FIG. 3 shows a view of a complete laminae on a scale of 50:1.

According to FIG. 3, the laminae 37, 38 are 2.6 mm long and 2.0 mm high. On the whole, they have the shape of trapezia and are made of hardened steel having a carbon content which allows laser welding. They are 0.3 mm thick, have a straight upper edge 42, a lower edge 43 which is parallel thereto and is symmetrical about the upper edge 42 and is shorter than this latter. Furthermore provided are lateral edges 44, 46 which are at an internal angle of approximately 60° to the upper edge 42. Between the upper edge 42 and the side edges 44, 46, there mediate radii of 0.5 mm, while radii of 0.3 mm mediate between the side edges 44, 46 and the lower edge 43. Radius centres 47, 48 for the 0,5 radius are shown in the drawing.

According to FIG. 2, the pins 39, 41 are of equal length, on the one hand, and somewhat longer than the thickness of the 0.4 mm thick lower zone of the slider 17, on the other hand. The pins 39, 41 have completely flat front surfaces. In the assembled state, their central axes are aligned with the radius centres 47, 48 of the laminae 37, 38. The circumference of the pins 39, 41 is fine-finished so as to give little friction so that the pins 39, 41 can rotate in the passage holes 31, 32 with ease but with little play. The pins 39, 41 are made of hardened steel, and the mating of the materials of the laminae 37, 38, on the one hand, and the pins 39, 41, on the other hand, is such that it allows laser welding.

According to FIG. 3, the upper edge 42 is altogether 2.6 mm long, and in the lower edge 43 this dimension is 0.68 mm.

In the area of the radius centres 47, 48, the laminae 37, 38 are rigidly welded together with the front surface areas of the pins 39, 41 by laser welding spots 49, 51, 52. The mean diameter of the laser welding spots 49, 51, 52 is substantially smaller than the diameter of the pins 39, 41.

As FIGS. 1 and 2 show, the laminae 37, 38 cover, with approximately half their height, the cutter bar 14 within its external edge 16. The other half is located outside thereof and covers, with the zones located therebehind, the lower thinner zone of the slider 17 with a sufficiently large area.

With the indicated construction, it is possible without difficulty to travel the radius of 0.32 mm indicated in FIG. 4. Furthermore, when the sliders 17 are in engagement with the sprocket wheel 12 in the zone thereof, there fits respectively one sprocket of the sprocket wheel 12 between the engagement surface 27 of a specific slider 17 and the surface 33 of the following slider.

Despite use being made of chain links of varying configuration, this construction allows a symmetrical application of the forces in the sprocket wheel 12, and the sprockets of the sprocket wheel 12 can have an optimum carrying width.

If a smooth external edge of the cutter bar is mentioned in the description, then this does not prevent the provision of a flat groove for the purpose of supplying a lubricant.

The invention allows not only relatively coarse cuts of 1 mm in width to be achieved. It is possible to construct the device so that it is narrower in width, thus also allowing saw cuts of, for example, 0.5 mm to be effected.

Above all, the invention also allows saw plungecuts to be effected.

The drive requirement is some tens of watts, approximately 20–60 watts.

What I claim is:

1. In a miniature blade device for motor-driven cutting instruments, which comprises a cutter bar, a sprocket wheel which is provided at the motor end of the cutter bar and is aligned with the cutter bar, an endless chain which comprises chain links and meshes with the sprocket wheel and is guided on the circumference of the cutter bar so as to be aligned with the central plane of the cutter bar, and sharpened, extremely narrow cutting elements provided on the outside of the chain links, the improvement wherein:
   (a) the cutter bar is a single-piece blade having a smooth external edge which guides the chain links parallel to the central plane, which chain links slide on the external edge;
   (b) apart from the sprocket wheel, no other guide wheel is provided;
   (c) two types of chain links are provided:
      (i) a slider having a base which slides on the external edge of the cutter bar and a lagging zone that is close to the base and is designed as an engagement surface for sprockets of the sprocket wheel, and two passage holes at right angles to the central plane, which are approximately evenly spaced from the base and are arranged so as to be close thereto,
      (ii) two approximately trapezium-shaped, very thin laminae, having tapering zones which are inwardly directed, arranged on both sides of the cutter bar so as to be parallel to the central plane thereof and so as to be at a short distance from the external surfaces and having corner zones of the widening portion of the trapezium shape which cover the passage holes leaving a small clearance, and two pins which pass through the passage holes and are rigidly connected to the corner zones;
   (d) the pins are connected to the corner zones of the laminae by laser welding.

2. A blade device as claimed in claim 1, in which every slider has a cutting element.

3. A blade device as claimed in claim 1, in which the cutting elements are saw teeth.

4. A blade device as claimed in claim 1, in which the cutting elements are knife blades.

5. A blade device as claimed in claim 1, in which the base of the slider extends up to the engagement surface in a straight and even manner.

6. A blade device as claimed in claim 1, in which the same engagement surface is provided on the slider in the preceding zone close to the base.

7. A blade device as claimed in claim 1, in which the edge distance of the passage holes from the base and the engagement surface of the slider is approximately equal to the thickness of the slider in that zone.

8. A blade device as claimed in claim 1, in which the edge distance of the passage holes from one another is approximately equal to double the thickness of the slider in that zone.

9. A blade device as claimed in claim 1, in which the laminae project approximately half-way above the half-way below the external edge of the cutter bar.

10. A blade device as claimed in claim 1, in which the pins are butt-welded to the corner zones of the laminae and serve as spacers.

* * * * *